US008324237B2

(12) United States Patent
Smith et al.

(10) Patent No.: US 8,324,237 B2
(45) Date of Patent: Dec. 4, 2012

(54) METHODS FOR THE TREATMENT AND PREVENTION OF INFLAMMATORY DISEASES

(76) Inventors: Charles D. Smith, Isle of Palms, SC (US); Kevin J. French, Harrisburg, PA (US); Lynn W. Maines, Hummelstown, PA (US)

(*) Notice: Subject to any disclaimer, the term of this patent is extended or adjusted under 35 U.S.C. 154(b) by 1346 days.

(21) Appl. No.: 11/437,988

(22) Filed: May 19, 2006

(65) Prior Publication Data

US 2006/0270630 A1 Nov. 30, 2006

Related U.S. Application Data

(60) Provisional application No. 60/682,895, filed on May 20, 2005.

(51) Int. Cl.
*A61K 31/44* (2006.01)
*A61K 31/425* (2006.01)

(52) U.S. Cl. ........................................ 514/285; 514/369

(58) Field of Classification Search .................. 514/285, 514/369

See application file for complete search history.

(56) References Cited

U.S. PATENT DOCUMENTS

| 7,338,961 B2 | 3/2008 | Smith et al. |
| 2004/0014635 A1 | 1/2004 | Vadas et al. |
| 2005/0100547 A1 | 5/2005 | Xia et al. |
| 2006/0270630 A1 | 11/2006 | Smith et al. |
| 2006/0270631 A1 | 11/2006 | Smith et al. |
| 2007/0032531 A1 | 2/2007 | Smith et al. |
| 2008/0167352 A1 | 7/2008 | Smith et al. |
| 2008/0279897 A1 | 11/2008 | Xia et al. |

FOREIGN PATENT DOCUMENTS

| WO | WO 03082322 | * 10/2003 |
| WO | 2006/135968 | 12/2006 |
| WO | 2006/135969 | 12/2006 |

OTHER PUBLICATIONS

O.H. Choi et al., Calcium Mobilization via sphingosine kinase in signalling by the FCeRI antigen receptor, Nature, vol. 380, pp. 634-636 (Apr. 18, 1996).
N. Kohl et al., Inhibition of farnesyltransferase induces regression of mammary and salivary carcinomas in ras transgenic mice, Nature Medicine, vol. 1, No. 8, pp. 792-797 (Aug. 1995).
Rask-Madsen, Soluble mediators and the interaction of drugs in IBD, Drugs of Today, vol. 34, No. 1, pp. 45-63 (1998).
P. Xia et al., Tumor Necrosis factor-alpha induces adhesion molecule expression through the sphingosine kinase pathway, Proc. Nat'l Acad. Sci. USA, vol. 95, pp. 14196-14201 (Nov. 1998).
K. Shimamura et al., Expression of adhesion molecules by sphingosine 1-phosphate and histamine in endothelial cells, European Journal of Pharmacology vol. 486, pp. 141-150 (2004).
W. Sandborn, Strategies for targeting tumour necrosis factor in IBD, Best Practice & Research Clinical Gastroenterology, vol. 17, No. 1, pp. 105-117 (2003).
M. Samuels and J. McDonald, Elementary School Children's Capacity to Choose Positive Diagnostic and Negative Diagnostic Tests, Child Development, vol. 73, No. 3, pp. 857-866 (May/Jun. 2002).
E. Prieschl et al., The Balance between Sphingosine and Sphingosine-1-phosphate Is Decisive for Mast Cell Activation after Fce Receptor I Triggering, J. Exp. Med., vol. 190, No. 1, pp. 1-8 (Jul. 5, 1999).
B. Pettus et al., The sphingosine kinase 1/sphingosine-1-phosphate pathway mediates COX-2 induction and PGE2 production in response to TNF-alpha, The FASEB Journal, vol. 17, pp. 1411-1421 (Aug. 2003).
J. Perez-Simon, Nonmyeloablative transplantation with or without alemtuzmab: comparison between 2 prospective studies in patients with lymphoproliferative disorders, Blood, vol. 100, No. 9, pp. 3121-3127 (Nov. 1, 2002).
M. Niwa et al., Tumor necrosis factor-alpha-mediated signal transduction in human neutrophils: involvement of sphingomyelin metabolites in the priming effect of TNF-alpha on the FMLP-stimulated superoxide production, Life Sciences, vol. 66, No. 3, pp. 245-256 (2000).
T. Megdish et al., The signal modulator protein 14-3-3 is a target of sphingosine- or N,N-dimethylsphingosine-dependent kinase in 3T3(A31) cells, Biochemical and Biophysical Research Communications, vol. 216, No. 3, pp. 739-747 (Nov. 22, 1995).
C. King et al., Sphingosine is a Novel Activator of 3-Phosphoinositide-dependent Kinase 1, The Journal of Biological Chemistry, vol. 275, No. 24, pp. 18108-18113 (Jun. 16, 2000).
A. Kihara et al., Long-chain Base Kinase Lcb4 Is Anchored to the Membrane through its Palmitoylation by Akr1, Molecular and Cell Biology, vol. 25, No. 21, pp. 9189-9197 (Nov. 2005).
S.-H. He, Key role of mast cells and their major secretory products in inflammatory bowel disease, World J. Gastroenterol., vol. 10, No. 3, pp. 309-318 (2004).
K. French et al., Discovery and Evaluation of Inhibitors of Human Sphingosine Kinase, Cancer Research, vol. 63, pp. 5962-5969 (Sep. 15, 2003).
K. Dressler et al., Tumor Necrosis Factor-alpha Activates the Sphingomyelin Signal Transduction Pathway in a Cell-Free System, Science, vol. 255, pp. 1715-1718 (Mar. 27, 1992).
A. Ammit et al., Sphingosine 1-phosphate modulates human airway smooth muscle cell functions that promote inflammation and airway remodeling in asthma, The FASEB Journal, vol. 15, pp. 1212-1214 (May 2001).
Y. Yatomi et al., Sphingosine-1-Phosphate: A Plately-Activating Spingolipid Released from Agonis-Stimulated Human Platelets, Blood, vol. 86, No. 1, pp. 193-202 (Jul. 1, 1995).

* cited by examiner

*Primary Examiner* — Renee Claytor

(74) *Attorney, Agent, or Firm* — McDonnell Boehnen Hulbert and Berghoff LLP

(57) ABSTRACT

The invention includes processes mainly for the treatment of a inflammatory diseases, such as inflammatory bowel disease, arthritis, atherosclerosis, asthma, allergy, inflammatory kidney disease, circulatory shock, multiple sclerosis, chronic obstructive pulmonary disease, skin inflammation, periodontal disease, psoriasis and T cell-mediated diseases of immunity, including allergic encephalomyelitis, allergic neuritis, transplant allograft rejection, graft versus host disease, myocarditis, thyroiditis, nephritis, systemic lupus erthematosus, and insulin-dependent diabetes mellitus. The processes involve treating a patient with a pharmaceutical composition containing an active ingredient that inhibits the activity of sphingosine kinase.

10 Claims, 16 Drawing Sheets

METHODS FOR THE TREATMENT AND PREVENTION OF INFLAMMATORY DISEASES

REFERENCE TO RELATED APPLICATIONS

This application is a non-provisional application claiming priority under 35 U.S.C. section 119(e) to provisional application No. 60/682,895 filed May 20, 2005, the contents of which are incorporated herein by reference.

GOVERNMENT SPONSORSHIP

This invention was made with government support Grants DK071395 and AR052261 awarded by the United States Public Health Service. Accordingly, the US government may have certain rights in this invention.

FIELD OF THE INVENTION

The present invention relates to methods useful for the treatment and/or prevention of inflammatory diseases. More specifically, the invention relates to the use of chemical compounds and pharmaceutical compositions that inhibit the enzymatic activity of human sphingosine kinase for the treatment and/or prevention of inflammatory diseases, such as inflammatory bowel disease, arthritis, atherosclerosis, asthma, allergy, inflammatory kidney disease, circulatory shock, multiple sclerosis, chronic obstructive pulmonary disease, skin inflammation, periodontal disease, psoriasis and T cell-mediated diseases of immunity, including allergic encephalomyelitis, allergic neuritis, transplant allograft rejection, graft versus host disease, myocarditis, thyroiditis, nephritis, systemic lupus erthematosus, and insulin-dependent diabetes mellitus.

BACKGROUND OF THE INVENTION

A. The Role of Sphingosine Kinase (SK) in Inflammatory Diseases.
1. Inflammatory Bowel Disease (IBD)

Inflammatory bowel disease (IBD) encompasses a group of disorders characterized by pathological inflammation of the lower intestine. Crohn's disease and ulcerative colitis are the best-known forms of IBD, and both fall into the category of "idiopathic" IBD because their etiologies remain to be elucidated, although proposed mechanisms implicate infectious and immunologic mediators. Studies on the etiology and therapy of IBD have been greatly facilitated by the development of several animal models that mimic the clinical and immunopathological disorders seen in humans. From studies with these models, it is clear that the full manifestations of IBD are dependent on synergy between the humoral and cellular immune responses. The notion that immune cells and cytokines play critical roles in the pathogenesis of IBD is well established; however, the molecular mechanisms by which this occurs are not yet clearly defined. As discussed below, cytokines that promote inflammation in the intestine afflicted with IBD, all activate a common mediator, sphingosine kinase (SK). Most prominently, tumor necrosis factor-α (TNFα) has been shown to play a significant role in IBD, such that antibody therapy directed against this cytokine, i.e. Remicade, may be a promising treatment (Sandborn, *Best Pract Res Clin Gastroenterol* 17: 105 (2003)). TNFα activates several processes shown to contribute to IBD and is necessary for both the initiation and persistence of the Th1 response. For example, TNFα has been shown act through the induction of nuclear factor kappa B (NFκB) which has been implicated in increasing the proinflammatory enzymes nitric oxide synthase (NOS) and cyclooxygenase-2 (COX-2). COX-2 has been shown to play a key role in the inflammation of IBDs through its production of prostaglandins, and oxidative stress such as that mediated by nitric oxide produced by NOS has also shown to exacerbate IBD inflammation.

A common pathway of immune activation in IBDs is the local influx of mast cells, monocytes, macrophages and polymorphonuclear neutrophils which results in the secondary amplification of the inflammation process and produces the clinical manifestations of the diseases (Rask-Madsen, *Drugs today* (*Barc.*) 34: 45 (1998)). This results in markedly increased numbers of mast cells in the mucosa of the ileum and colon of patients with IBD, which is accompanied by dramatic increases in TNFα (He, *World J Gastroenterology* 10 (3): 309 (2004)). Additional mast cell secretory products, including histamine and tryptase, may be important in IBDs. Therefore, it is clear that inflammatory cascades play critical roles in the pathology of IBDs.

The mechanisms and effects of the sphingolipid interconversion have been the subjects of a growing body of scientific investigation. Sphingomyelin is not only a structural component of cellular membranes, but also serves as the precursor for the potent bioactive lipids ceramide and sphingosine 1-phosphate (S1P). A ceramide: S1P rheostat is thought to determine the fate of the cell, such that the relative cellular concentrations of ceramide and S1P determine whether a cell proliferates or undergoes apoptosis. Ceramide is produced by the hydrolysis of sphingomyelin in response to inflammatory stresses, including TNFα, and can be hydrolyzed by ceramidase to produce sphingosine. Sphingosine is then rapidly phosphorylated by sphingosine kinase (SK) to produce S1P. Ceramidase and SK are also activated by cytokines and growth factors, leading to rapid increases in the intracellular levels of S1P and depletion of ceramide levels. This situation promotes cell proliferation and inhibits apoptosis. Deregulation of apoptosis in phagocytes is an important component of the chronic inflammatory state in IBDs, and S1P has been shown to protect neutrophils from apoptosis in response to Fas, TNFα and ceramide. Similarly, apoptosis of macrophages is blocked by S1P.

In addition to its role in regulating cell proliferation and apoptosis, S1P has been shown to have several important effects on cells that mediate immune functions. Platelets, monocytes and mast cells secrete S1P upon activation, promoting inflammatory cascades at the site of tissue damage (Yatomi et al., *Blood* 86: 193 (1995)). Activation of SK is required for the signaling responses, since the ability of TNFα to induce adhesion molecule expression via activation of NFκB is mimicked by S1P and is blocked by the SK inhibitor dimethylsphingosine (Xia et al., *Proc Natl Acad Sci USA* 95: 14196 (1998)). Similarly, S1P mimics the ability of TNFα to induce the expression of COX-2 and the synthesis of $PGE_2$, and knock-down of SK by RNA interference blocks these responses to TNFα but not S1P (Pettus et al., *Faseb J* 17: 1411 (2003)). S1P is also a mediator of $Ca^{2+}$ influx during neutrophil activation by TNFα and other stimuli, leading to the production of superoxide and other toxic radicals (Perez-Simon et al., *Blood* 100: 3121 (2002)).

A model for the roles of sphingolipid metabolites in the pathology of IBDs involves a combination of events in the colon epithelial cells and recruited mast cells, macrophages and neutrophils. Early in the disease, immunologic reactions or other activating signals promote the release of inflammatory cytokines, particularly TNFα from macrophages and mast cells. The actions of TNFα are mediated through its activation of S1P production. For example, TNFα induces S1P production in endothelial cells (Xia et al., *Proc Natl Acad Sci USA* 95: 14196 (1998)), neutrophils (Niwa et al., *Life Sci* 66: 245 (2000)) and monocytes by activation of sphingomyelinase, ceramidase and SK. S1P is a central player in the pathway since it has pleiotropic actions on the mucosal epithelial cells, macrophages, mast cells and neutrophils. Within the mucosal cells, S1P activates NFκB thereby inducing the expression of adhesion molecules, COX-2 resulting in $PGE_2$ synthesis, and NOS producing nitric oxide. Together, these chemoattractants and the adhesion molecules promote neutrophil infiltration into the mucosa. At the same time, S1P activates the neutrophils resulting in the release of oxygen free radicals that further inflame and destroy epithelial tissue. Similarly, S1P promotes the activation and degranulation of mast cells.

According to this model, two major targets for new anti-IBD therapies can be defined: TNFα and S1P. A great deal of effort has focused on developing anti-TNFα agents. The use of inhibitors of SK as anti-IBD agents has not been previously demonstrated. The following Examples demonstrate that SK inhibitors will be useful for the treatment and/or prevention of IBDs.

2. Arthritis

Rheumatoid arthritis (RA) is a chronic, systemic disease that is characterized by synovial hyperplasia, massive cellular infiltration, erosion of the cartilage and bone, and an abnormal immune response (Kohl et al., *Nat Med* 1: 792 (1995)). Studies on the etiology and therapy of rheumatoid arthritis have been greatly facilitated by the development of animal models that mimic the clinical and immunopathological disorders seen in humans. From studies in these models, it is clear that the full manifestations of RA are dependent on synergy between the humoral and cellular immune responses. The notion that immune cells, especially neutrophils, and cytokines play critical roles in the pathogenesis of arthritis is well established. However, the mechanisms by which this occurs are not fully elucidated.

The early phase of rheumatic inflammation is characterized by leukocyte infiltration into tissues, especially by neutrophils. In the case of RA, this occurs primarily in joints where leukocyte infiltration results in synovitis and synovium thickening producing the typical symptoms of warmth, redness, swelling and pain. As the disease progresses, the aberrant collection of cells invade and destroy the cartilage and bone within the joint leading to deformities and chronic pain. The inflammatory cytokines TNFα, IL-1β and IL-8 act as critical mediators of this infiltration, and these cytokines are present in the synovial fluid of patients with RA.

Leukocytes localize to sites of inflammatory injury as a result of the integrated actions of adhesion molecules, cytokines, and chemotactic factors. In lipopolysaccharide-induced arthritis in the rabbit, the production of TNFα and IL-1β in the initiative phase of inflammation paralleled the time course of leukocyte infiltration. The adherence of neutrophils to the vascular endothelium is a first step in the extravasation of cells into the interstitium. This process is mediated by selectins, integrins, and endothelial adhesion molecules, e.g. ICAM-1 and VCAM-1. Since TNFα induces the expression of ICAM-1 and VCAM-1 and is present in high concentrations in arthritic joints, it is likely that this protein plays a central role in the pathogenesis of the disease. This is supported by the clinical activity of anti-TNFα therapies such as Remicade. After adherence to the endothelium, leukocytes migrate along a chemoattractant concentration gradient. A further critical process in the progression of RA is the enhancement of the blood supply to the synovium through angiogenesis. Expression of the key angiogenic factor VEGF is potently induced by pro-inflammatory cytokines including TNFα. Together, these data point to important roles of TNFα, leukocytes, leukocyte adhesion molecules, leukocyte chemoattractants and angiogenesis in the pathogenesis of arthritic injury.

Early in the disease, immunologic reactions or other activating signals promote the release of inflammatory cytokines, particularly TNFα and IL-1β from macrophages and mast cells. Ceramide is produced by the hydrolysis of sphingomyelin in response to inflammatory stresses, including TNFα and IL-1β (Dressler et al., *Science* 255: 1715 (1992)). Ceramide can be further hydrolyzed by ceramidase to produce sphingosine which is then rapidly phosphorylated by SK to produce S1P. Ceramidase and SK are also activated by cytokines and growth factors, leading to rapid increases in the intracellular levels of S1P and depletion of ceramide levels. This situation promotes cell proliferation and inhibits apoptosis. Deregulation of apoptosis in phagocytes is an important component of the chronic inflammatory state in arthritis, and S1P has been shown to protect neutrophils from apoptosis in response to Fas, TNFα and ceramide. Similarly, apoptosis of macrophages is blocked by S1P.

In addition to its role in regulating cell proliferation and apoptosis, S1P is a central player in the pathway since it has pleiotropic actions on the endothelial cells, leukocytes, chondrocytes and synovial cells. Within the endothelial cells, S1P activates NFκB thereby inducing the expression of multiple adhesion molecules and COX-2 resulting in $PGE_2$ synthesis. Together, this chemoattractant and the adhesion molecules promote neutrophil infiltration into the synovium. At the same time, S1P directly activates the neutrophils resulting in the release of oxygen free radicals that destroy joint tissue (Perez-Simon et al., *Blood* 100: 3121 (2002)). Progression of RA is associated with a change from a Th1 to a Th2 environment, and sphingosine is selectively inhibitory toward Th1 cells. Consequently, inhibiting the conversion of sphingosine to S1P should attenuate the progression of the disease. Platelets, monocytes and mast cells secrete S1P upon activation, promoting inflammatory cascades at the site of tissue damage (Yatomi et al., *Blood* 86: 193 (1995)). S1P also promotes the secretion of proteases from chondrocytes that contribute to joint destruction. Finally, S1P-mediated expression of VEGF promotes the angiogenesis necessary to support the hyperproliferation of synovial cells.

According to this model, two major targets for new anti-RA therapies can be defined: TNFα and S1P. The use of inhibitors of SK as anti-RA agents has not been previously demonstrated. The following Examples demonstrate that SK inhibitors prevent TNFα-mediated activation of endothelial cells and inhibit the progression of arthritis in vivo, making these compounds useful for the treatment and/or prevention of RA.

3. Atherosclerosis

Atherosclerosis is a complex vascular disease that involves a series of coordinated cellular and molecular events characteristic of inflammatory reactions. In response to vascular injury, the first atherosclerotic lesions are initiated by acute inflammatory reactions, mostly mediated by monocytes, platelets and T lymphocytes. These inflammatory cells are activated and recruited into the subendothelial vascular space through locally expressed chemotactic factors and adhesion molecules expressed on endothelial cell surface. Continuous recruitment of additional circulating inflammatory cells into the injured vascular wall potentiates the inflammatory reaction by further activating vascular smooth muscle (VSM) cell migration and proliferation. This chronic vascular inflammatory reaction leads to fibrous cap formation, which is an oxidant-rich inflammatory milieu composed of monocytes/macrophages and VSM cells. Over time, this fibrous cap can be destabilized and ruptured by extracellular metalloproteinases secreted by resident monocytes/macrophages. The ruptured fibrous cap can easily occlude vessels resulting in acute cardiac or cerebral ischemia. This underlying mechanism of atherosclerosis indicates that activation of monocyte/macrophage and VSM cell migration and proliferation play critical roles in the development and progression of atherosclerotic lesions. Importantly, it also suggests that a therapeutic approach that blocks the activities of these vascular inflammatory cells or smooth muscle cell proliferation should be able to prevent the progression and/or development of atherosclerosis.

SK is highly expressed in platelets allowing them to phosphorylate circulating sphingosine to produce S1P. In response to vessel injury, platelets release large amounts of S1P into the sites of injury which can exert mitogenic effects on VSM cells by activating S1P receptors. S1P is also produced in activated endothelial and VSM cells. In these cells, intracellularly produced S1P functions as a second messenger molecule, regulating $Ca^{2+}$ homeostasis associated with cell proliferation and suppression of apoptosis. Additionally, deregulation of apoptosis in phagocytes is an important component of the chronic inflammatory state of atherosclerosis, and S1P protects granulocytes from apoptosis. Together, these studies indicate that activation of SK alters sphingolipid metabolism in favor of S1P formation, resulting in pro-inflammatory and hyper-proliferative cellular responses.

In addition to its role in regulating cell proliferation and apoptosis, S1P has been shown to have several important effects on cells that mediate immune functions. Platelets and monocytes secrete cytokines, growth factors and S1P upon activation, promoting inflammatory cascades at the site of tissue damage. For example, TNFα has been shown to act through the induction of nuclear factor kappa B (NFκB), which has been implicated in increasing the proinflammatory enzymes nitric oxide synthase (NOS) and cyclooxygenase-2 (COX-2). COX-2 may play a key role in the inflammation of atherosclerosis through its production of prostaglandins, and oxidative stress such as that mediated by nitric oxide produced by NOS has also shown to exacerbate inflammation. Activation of SK is required for signaling responses since the ability of inflammatory cytokines to induce adhesion molecule expression via activation of NFκB is mimicked by S1P. Similarly, S1P mimics the ability of TNFα to induce the expression of COX-2 and the synthesis of $PGE_2$, and knockdown of SK by RNA interference blocks these responses to TNFα but not S1P. S1P is also a mediator of $Ca^{2+}$ influx during granulocyte activation, leading to the production of superoxide and other toxic radicals. SK is an emerging molecular target for inflammatory diseases, including atherosclerosis.

According to this model, SK is a major target for new anti-atherosclerosis therapies. The use of inhibitors of SK as anti-atherosclerosis agents has not been previously demonstrated. The following Examples demonstrate that SK inhibitors prevent cytokine-mediated activation of endothelial cells and leukocytes. This will prevent the deleterious activation of leukocytes, as well as prevent infiltration and smooth muscle cell hyperproliferation, making these compounds useful for the treatment and/or prevention of atherosclerosis.

4. Asthma

The physiological endpoint in asthma pathology is narrowing of the bronchial tubes due to inflammation. In a large portion of asthma cases, the inflammation is initiated and later amplified by exposure to allergens. Upon inhalation, these allergens, bind to circulating IgE and then bind to the high-affinity FcεRI surface receptors expressed by inflammatory cells residing in the bronchial mucosa. This extracellular binding leads to a cascade of signaling events inside the inflammatory cells, culminating in activation of these cells and secretion of multiple factors that trigger the cells lining the bronchial airways to swell, resulting in restricted bronchial tubes and decreased air exchange. The inflammation process in response to the initial exposure to allergen may not completely subside. Furthermore, additional exposures may lead to an exaggerated response called bronchial hyper-reactivity. This hyper-reactive state can lead to a permanent condition of restricted airways through airway remodeling. Consequently, unchecked inflammatory responses to initial allergen exposure may result in chronic inflammation and permanent bronchiolar constriction. Therefore, inhibiting or diminishing this exaggerated inflammation would likely decrease the symptoms associated with asthma.

Many studies have revealed the involvement of mast cells in the inflammatory process leading to asthma, and SK has been shown to be involved in allergen-stimulated mast cell activation, a critical step in the bronchial inflammatory process. In rat basophilic leukemia RBL-2H3 cells, IgE/Ag binding to the high-affinity FcεRI receptor leads to SK activation and conversion of sphingosine to S1P (Choi et al., *Nature* 380: 634 (1996)). The newly formed S1P increases intracellular calcium levels, which is necessary for mast cell activiation. Alternately, high concentrations of sphingosine decreased IgE/Ag exposure-mediated leukotriene synthesis and diminished cytokine transcription and secretion (Prieschl et al., *J Exp Med* 190: 1 (1999)).

In addition to the key role of SK and S1P in mast cell activation, S1P also has direct effects on downstream signaling in the asthma inflammation pathway. Ammit and coworkers demonstrated increased S1P levels in bronchoalveolar lavage (BAL) fluid collected from asthmatic patients 24 hours after allergen challenge compared with non-asthmatic subjects (Ammit et al., *Faseb J* 15:1212 (2001)). In conjunction with the finding that activated mast cells produce and secrete S1P, these results reveal a correlation between S1P and the asthmatic inflammatory response. To evaluate a possible role of SK and S1P exposure to cell response, ASM cultures were grown in the presence of S1P (Ammit et al., *Faseb J* 15: 1212 (2001)). Furthermore, airway smooth muscle (ASM) cells are responsive to S1P- and SK-dependent stimuli, such as TNFα and IL-1β. Treatment with S1P increases phosphoinositide hydrolysis and intracellular calcium mobilization, both of which promote ASM contraction. Furthermore, S1P treatment increases DNA synthesis, cell number and accelerated progression of ASM cells from $G_1$ to S phase.

In addition to the direct effects on ASM cells, S1P also regulates secretion of cytokines and expression of cell adhesion molecules that amplify the inflammatory response through leukocyte recruitment and facilitating extracellular component interaction. S1P, like TNFα, induces IL-6 secretion and increases the expression of cell adhesion molecules such as VCAM-1, ICAM-1 and E-selectin (Shimamura et al., *Eur J Pharmacol* 486: 141 (2004)).

According to this model, SK is a major target for new anti-asthma therapies. The use of inhibitors of SK as anti-asthma agents has not been previously demonstrated. The following Examples demonstrate that SK inhibitors prevent cytokine-mediated activation of leukocytes and other cells. This will prevent the deleterious activation of leukocytes, as well as prevent airway smooth muscle cell hyperproliferation, making these compounds useful for the treatment and/or prevention of asthma.

5. Other Inflammatory Diseases

Chronic obstructive pulmonary disease (COPD), like asthma, involves airflow obstruction and hyperresponsiveness that is associated with aberrant neutrophil activation in the lung tissue. This is clinically manifested as chronic bronchitis, fibrosis or emphysema, which together make up the fourth leading cause of death in the United States. Since activation of inflammatory cells by chemical insults in COPD occurs through NFκB-mediated pathways similar to those activated during asthma, it is likely that inhibitors of SK will also be useful for the treatment and/or prevention of COPD.

Inflammation is involved in a variety of skin disorders, including psoriasis, atopic dermatitis, contact sensitivity and acne, which affect more than 20% if the population. Although topical corticosteroids have been widely used, their adverse effects prevent long-term use. Since the inflammatory responses typically involve aberrant activation of signaling pathways detailed above, it is likely that inhibitors of SK will also be useful for the treatment of these skin diseases.

A variety of diseases including allergic encephalomyelitis, allergic neuritis, transplant allograft rejection, graft versus host disease, myocarditis, thyroiditis, nephritis, systemic lupus erthematosus, and insulin-dependent diabetes mellitus can be induced by inappropriate activation of T cells. Common features of the pathogenesis of these diseases include infiltration by mononuclear cells, expression of CD4 and CD8 autoreactive T cells, and hyperactive signaling by inflammatory mediators such as IL-1, IL-6 and TNFα. Since the inflammatory responses typically involve aberrant activation of signaling pathways detailed above, it is likely that inhibitors of SK will also be useful for the treatment of these T cell-mediated diseases of immunity.

B. Sphingosine Kinase Enzymology and Pharmacology.

Sphingosine kinase catalyzes the production of S1P in cells. RNA encoding SK is detected in most tissues, with higher levels in lung and spleen. A number of studies have shown that a variety of proliferative factors, including PKC activators, fetal calf serum and platelet-derived growth factor, EGF, and TNFα (Xia et al., *Proc Natl Acad Sci USA* 95: 14196 (1998)) rapidly elevate cellular SK activity.

In spite of the high level of interest in sphingolipid-mediated signaling, there are very few known inhibitors of the enzymes of this pathway. Pharmacological studies to date have used three compounds to inhibit SK activity: dimethylsphingosine (DMS), D,L-threo-dihydrosphingosine and N,N,N-trimethylsphingosine. However, these compounds are not specific inhibitors of SK and have been shown to affect protein kinase C (Kihara et al., *Mol Cell Biol* 25: 9189 (2005)), sphingosine-dependent protein kinase (Megidish et al., *Biochem Biophys Res Commun* 216: 739 (1995)), 3-phosphoinositide-dependent kinase (King et al., *J Biol Chem* 275: 18108 (2000)), and casein kinase II (Samuels et al., *Child Dev* 73: 857 (2002)). Therefore, improved inhibitors of SK are required not only for basic research, but also as lead compounds for developing novel drugs. To this end, a series of structurally novel inhibitors of SK was identified (French et al., *Cancer Res* 63: 5962 (2003)). These compounds inhibit endogenous S1P formation in intact cancer cells while inducing apoptosis, and demonstrate a high degree of selectivity for SK versus other lipid and protein kinases. We have developed additional SK inhibitors that have activity in both cell and animal models. As demonstrated in the following Examples, these SK inhibitors can be chronically administered without systemic toxicity. Because of their excellent pharmacological properties, these new SK inhibitors provide agents for the practice of therapies that inhibit SK activity in target cells within an animal.

SUMMARY OF THE INVENTION

The invention relates to methods for the use of compounds and pharmaceutical compositions for the treatment and prevention of inflammatory diseases. The compounds, and the active ingredient of the compositions, inhibit the activity of human sphingosine kinase.

DESCRIPTION OF THE PREFERRED EMBODIMENTS

Figure 1:
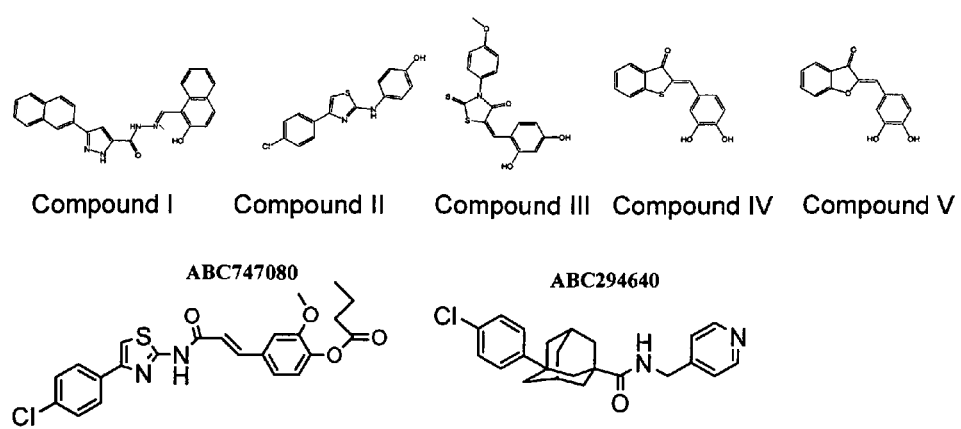
FIG. 1. SK inhibitors. Representative compounds with SK inhibitory activity are shown.

The present invention provides methods for the use of compounds and pharmaceutical compositions for the treatment of inflammatory diseases. The chemical compounds and pharmaceutical compositions of the present invention may be useful in the therapy of inflammatory diseases, such as inflammatory bowel disease, arthritis, atherosclerosis, asthma, allergy, inflammatory kidney disease, circulatory shock, multiple sclerosis, chronic obstructive pulmonary disease, skin inflammation, periodontal disease, psoriasis and T cell-mediated diseases of immunity, including allergic encephalomyelitis, allergic neuritis, transplant allograft rejection, graft versus host disease, myocarditis, thyroiditis, nephritis, systemic lupus erthematosus, and insulin-dependent diabetes mellitus.

The compounds and pharmaceutical compositions to be used in the present invention can be used in various protocols for treating animals, including humans. In one embodiment of the methods of the present invention, SK in target cells or tissues in an animal undergoing chemotherapy is inhibited by administering to the animal a pharmaceutical composition in an amount effective to inhibit SK in the target cells or tissues of the animal.

In a particularly preferred embodiment of the use of the methods of the present invention, the compounds or compositions can be used for treating inflammation in a patient requiring such treatment, by administering the compound or composition to a patient in an amount effective to inhibit the activation of target cells of said patient. This method would involve administering to a patient with an inflammatory disease a composition in an amount effective to prevent the actions of inflammatory growth factors or other stimuli on endothelial cells, immune cells, luminal epithelial cells, vascular or airway smooth muscle cells and/or leukocytes, including mast cells, neutrophils, monocytes, macrophages, platelets and T-lymphocytes.

In another particularly preferred embodiment of the use of the methods of the present invention, the compounds or compositions can be used in a method for treating an inflammatory bowel disease in a patient requiring such treatment, by administering the composition to a patient in an amount effective to inhibit the aberrant activation of luminal epithelial cells, macrophages, mast cells and/or neutrophils. For example, these methods can be used for treating a patient with ulcerative colitis or Crohn's Disease. This method would involve administering to the patient a compound or composition in an amount effective to inhibit SK activity in the luminal epithelial cells, macrophages, mast cells and/or neutrophils.

In another particularly preferred embodiment of the use of the methods of the present invention, the compounds or compositions can be used in a method for treating arthritis in a patient requiring such treatment, by administering the composition to a patient in an amount effective to inhibit the aberrant activation of macrophages, mast cells, neutrophils, endothelial cells, chondrocytes and/or synovial cells. For example, these methods can be used for treating a patient with rheumatoid arthritis. This method would involve administering to the patient a compound or composition in an amount effective to inhibit SK activity in macrophages, mast cells, neutrophils, endothelial cells, chondrocytes and/or synovial cells.

In another particularly preferred embodiment of the use of the methods of the present invention, the compounds or compositions can be used in a method for treating atherosclerosis in a patient requiring such treatment, by administering the composition to a patient in an amount effective to inhibit the aberrant activation of platelets, macrophages, monocytes, vascular endothelial cells, and/or vascular smooth muscle cells. This method would involve administering to the patient a compound or composition in an amount effective to inhibit SK activity in platelets, macrophages, monocytes, vascular endothelial cells, and/or vascular smooth muscle cells.

In another particularly preferred embodiment of the use of the methods of the present invention, the compounds or compositions can be used in a method for treating bronchial hypersensitivity in a patient requiring such treatment, by administering the composition to a patient in an amount effective to inhibit the aberrant activation of mast cells, neutrophils, eosinophils and/or airway smooth muscle cells. For example, these methods can be used for treating a patient with asthma. This method would involve administering to the patient a compound or composition in an amount effective to inhibit SK activity in mast cells, neutrophils, eosinophils and/or airway smooth muscle cells.

In another particularly preferred embodiment of the use of the methods of the present invention, the compounds or compositions can be used in a method for treating chronic obstructive pulmonary disease, skin inflammation or a T cell-mediated disease of immunity, including allergic encephalomyelitis, allergic neuritis, transplant allograft rejection, graft versus host disease, myocarditis, thyroiditis, nephritis, systemic lupus erthematosus, and insulin-dependent diabetes mellitus, in a patient requiring such treatment, by administering the composition to a patient in an amount effective to inhibit the aberrant activation of T cells. For example, these methods can be used for treating a patient with chronic obstructive pulmonary disease, skin inflammation or a T cell-mediated disease of immunity, including allergic encephalomyelitis, allergic neuritis, transplant allograft rejection, graft versus host disease, myocarditis, thyroiditis, nephritis, systemic lupus erthematosus, and insulin-dependent diabetes mellitus. This method would involve administering to the patient a compound or composition in an amount effective to inhibit SK activity in T cells.

In view of the beneficial effect of inhibiting SK, it is anticipated that the methods of the present invention will be useful not only for therapeutic treatment following the onset of disease, but also for the prevention of disease in animals, including humans. The methods described herein will be essentially the same whether the compounds or pharmaceutical compositions are being administered for the treatment or prevention of disease.

While the invention has been particularly shown and described with reference to preferred embodiments thereof, it will be understood by those skilled in the art that various alterations in form and detail may be made therein without departing from the spirit and scope of the invention. In particular, the specific method of use of the SK inhibitory compounds and compositions can vary significantly without departing from the discovered methods. Additionally, methods for the treatment of additional diseases that involve undesired activation of inflammatory mechanisms within particular cells of the patient are considered to be within the scope of the following claims.

The Examples, which follow, are illustrative of specific embodiments of the invention, and various uses thereof. They are set forth for explanatory purposes only, and are not to be taken as limiting the invention.

EXAMPLE 1

Identification of SK Inhibitors

An assay for screening for inhibitors of SK has been established (French et al., *Cancer Res* 63: 5962 (2003)). A chemical library totaling approximately 16,000 compounds was screened for inhibition of SK. Representative active compounds from four chemotypes of SK inhibitors, designated herein as Compounds I-IV, are shown in FIG. 1. The compounds ABC747080 and ABC294640 (FIG. 1) also inhibit SK.

EXAMPLE 2

Inhibition of Endogenous SK Activity by SK Inhibitors

Figures 2A, 2B:
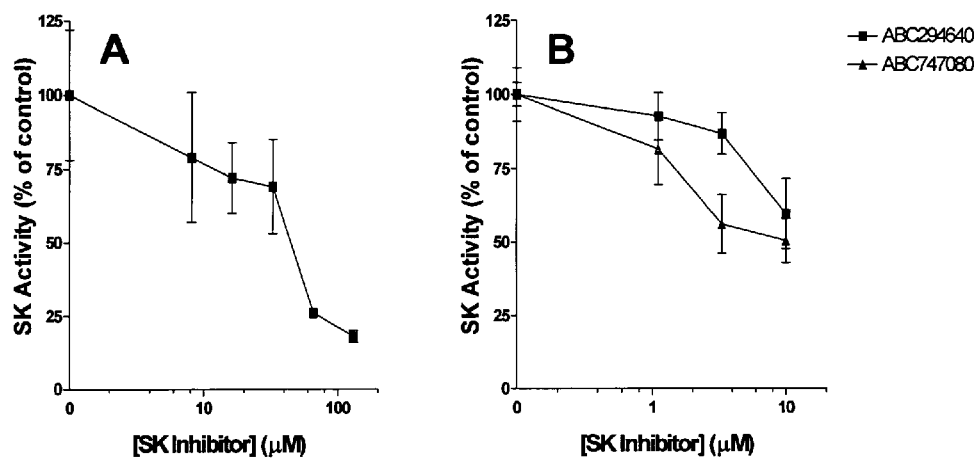
FIG. 2. Inhibition of cellular SK by ABC294640 and ABC747080. Rat IEC6 cells (Panel A) or human endothelial cells (Panel B) were incubated with the indicated concentration of ABC294640 (■) or ABC747080 (▲) before the addition of 0.4 μCi of [$^3$H]sphingosine. After 15 minutes, cells were lysed and extracted with chloroform:methanol, and the amounts of [$^3$H]sphingosine in the organic phase and [$^3$H] S1P in the aqueous phase were then determined. Values represent the mean±sd SK activity in triplicate samples in a typical experiment.

A cell-based assay in which the phosphorylation of exogenously added [$^3$H]sphingosine to [$^3$H]S1P by endogenous SK can be quantified (French et al., *Cancer Res* 63: 5962 (2003)) was used to evaluate the effects of test compounds on the activity of SK in intact cells. In this assay, cells are incubated with [$^3$H]sphingosine for an appropriate period of time, and then [$^3$H]sphingosine and [$^3$H]S1P (formed by endogenous SK activity) are separated by extraction and levels of both species are determined by scintillation counting. We have used a number of cell lines in this assay to confirm that the SK inhibitors are active in multiple intact cell systems. For example, human umbilical vein endothelial cells (HUVECs) are commonly used as a model of human vasculature. Additionally, rat IEC6 cells are commonly used as a model of intestinal epithelial cells. As demonstrated in FIG. 2, the SK inhibitors reduce cellular levels of S1P synthesis human endothelial cells and rat IEC6 cells. ACB294640 and ABC747080 each caused dose-dependent suppression of SK activity in each of the cell types, with the endothelial cells being somewhat more sensitive than the epithelial cells.

Figure 3:
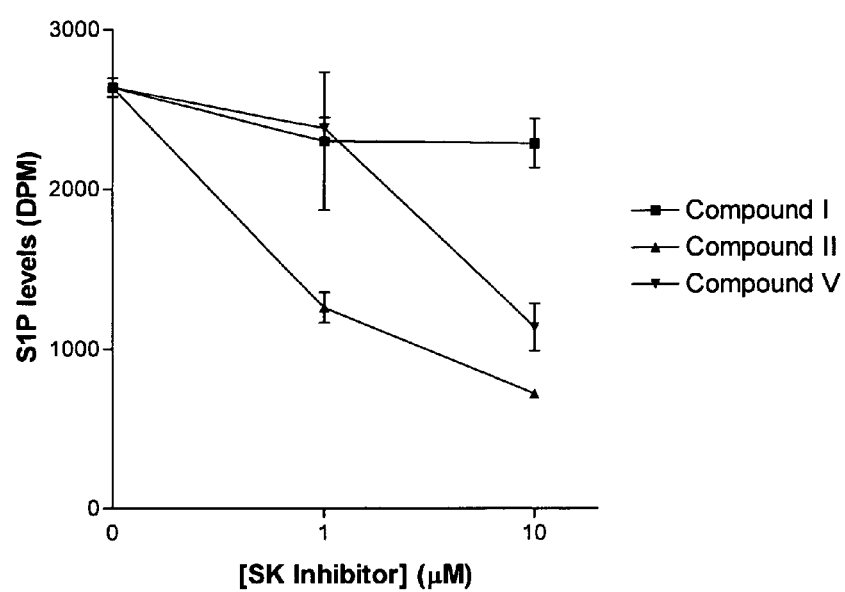
FIG. 3. Inhibition of S1P production in HUVECs by additional SK inhibitors. HUVECs were treated with the indicated concentrations of Compound I, II or V for 24 hours. SK activity was measured by adding [$^3$H]sphingosine and determining its conversion to [3H]S1P. Values represent the mean±SD of duplicate samples.

In additional experiments shown in FIG. 3, the effects of several SK inhibitors on [$^3$H]S1P levels in HUVECs were demonstrated. Compounds II and V caused dose-dependent reductions in the cellular levels of S1P demonstrating that these compounds also effectively inhibit SK activity in HUVECs.

In additional experiments summarized in Table 1, the effects of Coumpound II and ABC747080 on S1P production in multiple cell lines involved in the inflammatory signaling cascade were tested. Specifically, HUVECs, human chondrocytes (HC), and human synovial cells from a patient with RA (HFLS-RA) were examined. Both Compound II and ABC747080 were capable of inhibiting endogenous SK activity in each of these types of cells, with Compound II demonstrating higher potency.

TABLE 1

Compound II and ABC747080 inhibit S1P formation in cells modulating the inflammatory response in arthritis. Values represent drug concentrations (in μM) that decrease S1P formation by 50%.

| Test Compound | HUVECs | HCs | HFLS-RA cells |
|---|---|---|---|
| Compound II | 0.2 | 0.36 | 0.19 |
| ABC747080 | 9.2 | 8.5 | 12 |

EXAMPLE 3

Inhibition of TNFα-Induction of NFκB by SK Inhibitors

Figure 4:
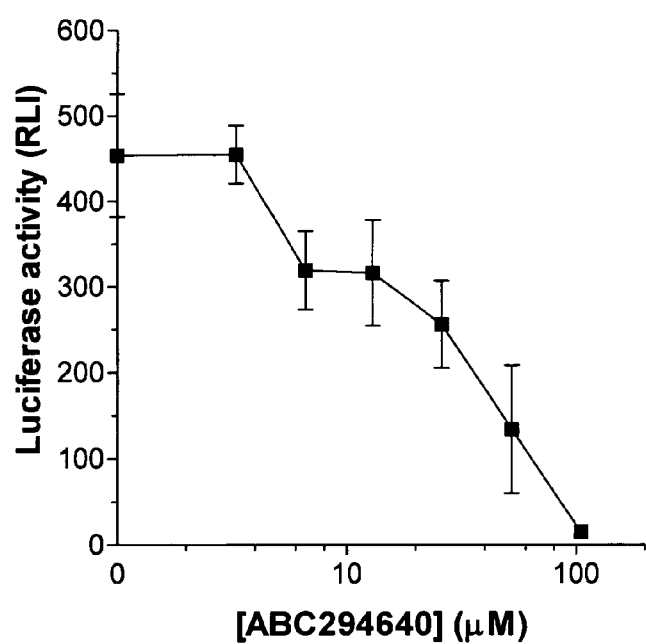
FIG. 4. Inhibition of TNFα-induced activation of NFκB by ABC294640. Fibroblasts transfected with a TNFα-responsive promoter linked to luciferase were treated with the indicated concentrations of ABC294640 and then treated with TNFα for 6 hours. The amount of luciferase expressed by the cells was then measured by luminescence. Values represent the mean±sd luciferase activity in triplicate samples in a typical experiment.

The excellent aqueous solubility of ABC294640 allowed it to be evaluated in an NFκB reporter cell line (FIG. 4). Fibroblasts transfected with an NFκB response element linked to luciferase produce high levels of luciferase upon exposure to TNFα. Activation of NFκB by TNFα was dose-dependently suppressed by the SK inhibitor, ABC294640.

EXAMPLE 4

Inhibition of TNFα-Induced Adhesion Molecule Expression by SK Inhibitors

Like endothelial cells in the body, HUVECs will proliferate in response to several growth factors, and will respond to inflammatory cytokines such as TNFα and IL-1β. Western analyses were conducted with human endothelial cells to evaluate the effects of the SK inhibitors on signaling proteins known to be regulated by TNFα. In these experiments, the cells were serum-starved for 24 hours and then exposed to TNFα (100 ng/mL) for 6 hours. Cell lysates from treated cells were assayed for the adhesion molecules ICAM-1 and VCAM-1. TNFα caused marked increases in the expression levels of adhesion proteins involved in leukocyte recruitment, including ICAM-1 and VCAM-1. These effects of TNFα were inhibited by treating the cells with either ABC294640 or ABC747080, such that the induction of both proteins was completely abrogated by 25 μM ABC294640.

EXAMPLE 5

Inhibition of TNFα-Induced Prostaglandin Synthesis by SK Inhibitors

Figures 5A, 5B:
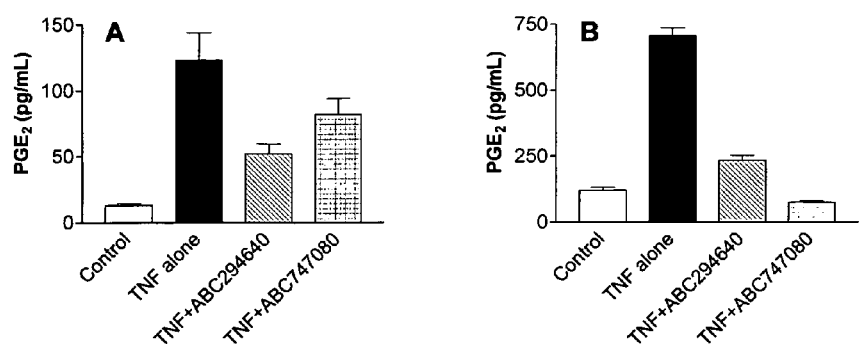
FIG. 5. Inhibition of TNFα-induced Cox-2 activity by SK inhibitors. Rat IEC6 cells (Panel A) or human endothelial cells (Panel B) were incubated for 18 hours with dimethylsulfoxide (DMSO) as a solvent control, or 100 ng of TNFα/mL in the presence of DMSO or 10 μg/mL of ABC294640 or ABC747080. Levels of PGE$_2$ secreted into the medium were quantified by ELISA. Values represent the mean±sd for triplicate samples in a typical experiment.

To determine the effects of the SK inhibitors on Cox-2 activity, an ELISA assay was used to measure $PGE_2$ production by IEC6 rat intestinal epithelial cells and human endothelial cells treated with TNFα. Exposure of either type of cell to TNFα resulted in marked increases in Cox-2 activity, measured as the production of $PGE_2$ (FIG. 5). This induction of Cox-2 activity by TNFα was strongly suppressed by ABC294640 or ABC747080.

EXAMPLE 6

Inhibition of Leukocyte Function by SK Inhibitors

Figure 6:
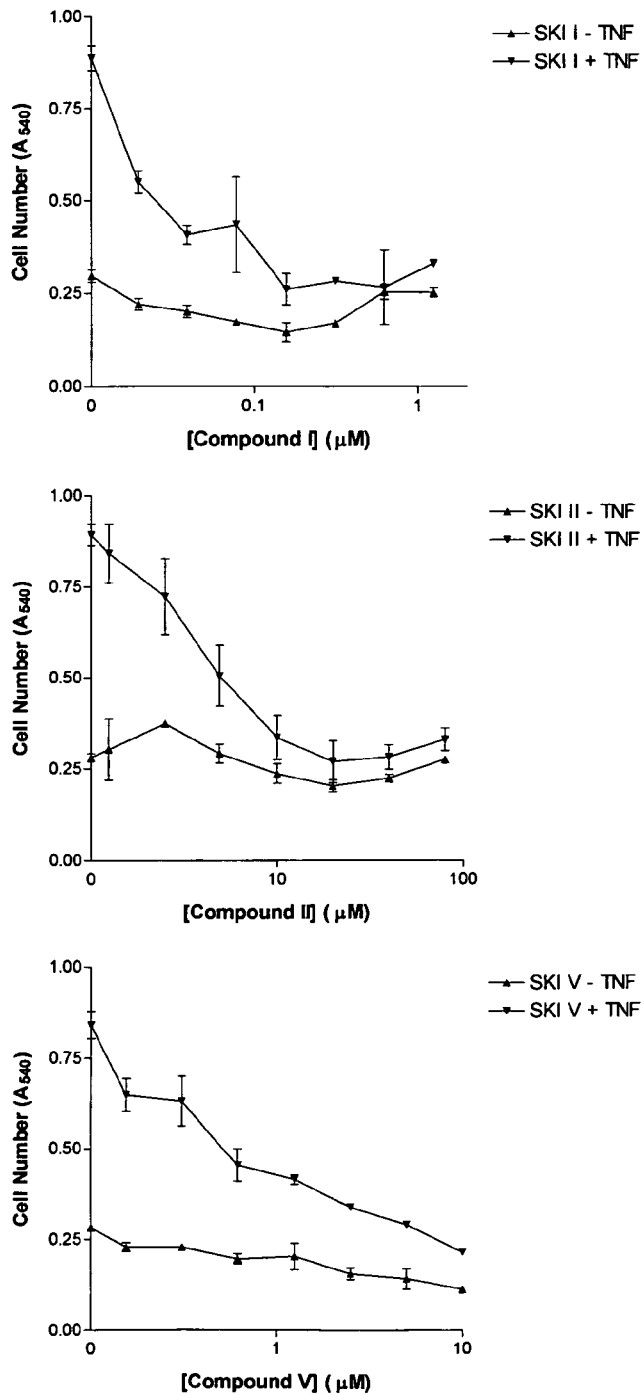
FIG. 6. Inhibition of TNFα-induced HL-60 cell proliferation by SK inhibitors. HL-60 cells were serum-starved for 18 hours and then left untreated (▲) or treated with 25 ng of TNFα/ml (▼) in the presence of the indicated concentrations of Compound I, II or V. After 72 hours, the number of cells in each treatment group was quantified.

As discussed above, aberrant activation of leukocytes is a central feature of many inflammatory diseases. Because of the roles of S1P in promoting leukocyte proliferation, we examined the effects of several SK inhibitors on the proliferation of HL-60 (human promyelocytic leukemia) cells. As indicated in FIG. 6, treatment of serum-starved HL-60 cells with TNFα supported a nearly 3-fold increase in the rate of cell proliferation, compared with control cells. Treatment of TNFα-stimulated cells with Compound I, II or V caused dose-dependent reductions in HL-60 cell proliferation. Compound I was particularly effective, completely blocking the effects of TNFα at concentrations of 0.2 μM or greater.

Overall, these data demonstrate that inhibition of SK will be effective in blocking the inflammatory cascade in cells initiated by TNFα. This is expected to alleviate the pathology of diseases several inflammatory diseases, including IBD, arthritis, atherosclerosis and asthma.

EXAMPLE 7

Maximum Tolerated Dose of SK Inhibitors

ABC747080 and ABC294640 have been synthesized in amounts sufficient for characterization of their toxicity, pharmacokinetics and in vivo efficacies. The compounds are soluble to at least 15 mg/ml in 50% dimethylsulfoxide: 50% phosphate-buffered saline (DMSO:PBS) for intraperitoneal (IP) administration or Polyethylene glycol-400 (PEG400) for oral dosing. Acute toxicity studies using IP dosing demonstrated no immediate or delayed toxicity in female Swiss-Webster mice treated with up to at least 50 mg/kg for ABC747080 or ABC294640. Repeated injections in the same mice every other day over 15 days showed similar lack of toxicity. Each of the compounds could also be administered orally to mice at doses up to at least 100 mg/kg without noticeable toxicity. Therefore, these compounds were suitable for chronic in vivo treatments.

EXAMPLE 8

Pharmacokinetics of SK Inhibitors

Detailed pharmacokinetic studies were performed on ABC747080 and ABC294640 dissolved in PEG400 or 0.375% Tween-80, respectively. Female Swiss-Webster mice were dosed with 50 mg/kg ABC294640 either intravenously or orally, or 100 mg/kg ABC747080 orally. Mice were anesthetized and blood was removed by cardiac puncture at time points ranging from 1 minute to 8 hours. Concentrations of ABC747080 and ABC294640 were quantified using liquid-liquid extraction and reverse phase HPLC coupled to an ion trap quadrapole mass spectrometer. Control blood samples were spiked with known amounts of internal standard and analyte to identify compound-specific peaks and to develop standard curves for quantification. Pharmacokinetic parameters were calculated using the WINNONLIN analysis software package (Pharsight). Non-compartmental and compartmental models were tested, with the results from the best fitting models shown in Table 2.

TABLE 2

Pharmacokinetic data for SK inhibitors.

| Compound | Route | Dose (mg/kg) | $AUC_{0\to\infty}$ (μg * h/ml) | $AUC_{0\to\infty}$ (μM * h) | $T_{max}$ (h) | $C_{max}$ (μg/ml) | $C_{max}$ (μM) | $T_{1/2}$ (h) |
|---|---|---|---|---|---|---|---|---|
| ABC294640 | IV | 50 | 56.9 | 137 | 0 | 31.1 | 74 | 1.4 |
| ABC294640 | Oral | 50 | 37.5 | 90.1 | 0.25 | 8 | 19 | 4.5 |
| ABC747080 | Oral | 100 | 475 | 1500 | 1 | 15 | 33 | 32 |

For both compounds, blood levels exceeded the $IC_{50}$ for inhibition of SK activity during the entire study. ABC747080 demonstrated excellent PK properties, with large Area Under the Curve (AUC) and $C_{max}$ (maximum concentration reached in the blood) values. ABC294640 demonstrated desirable PK properties as well, with acceptable half life and $C_{max}$ values. Comparison of oral versus intravenous pharmacokinetics of ABC294640 revealed very good oral bioavailability properties (F=AUC (oral)/AUC (iv)=0.66). These results demonstrate that both ABC747080 and ABC294640 have excellent drug properties, specifically good oral availability with low toxicity.

EXAMPLE 9

In Vivo Effects of SK Inhibitors in an Acute Model of Inflammatory Bowel Disease We have conducted experiments with SK inhibitors using the dextran sulfate sodium (DSS) model of IBD. In these experiments, male C57BL/6 mice were provided with standard rodent diet and water ad libitum. After their acclimation, the animals were randomly divided into groups of 5 or 6 for DSS (40,000 MW from ICN Biomedicals, Inc., Aurora, Ohio)—and drug-treatment. The SK inhibitors were dissolved in PEG400, and given once daily by oral gavage in a volume of 0.1 mL per dose. Dipentum, an FDA-approved anti-colitis drug whose active ingredient, olsalazine, is converted to 5-aminosalicylic acid in vivo, was used as a positive control. The mice were given normal drinking water or 2% DSS and treated orally with an SK inhibitor or Dipentum at a dose of 50 mk/kg daily. The body weight of each animal was measured each day, and the Disease Activity Index (DAI) was scored for each animal on Days 4-6. On Day 6, the animals were sacrificed by cervical dislocation and the entire colon was removed and measured to the nearest 0.1 cm. Portions of the colons were then fixed, sectioned and their histologies were assessed on a blinded basis to determine their Histology Score. Other portions of the colons were used for biochemical analyses of inflammation markers.

The DAI monitors weight loss, stool consistency and blood in the stool and is a measure of disease severity. Animals receiving normal drinking water and PEG as a solvent control had very low DAIs throughout the experiment (FIG. 6). Exposure of the mice to DSS in their drinking water markedly induced IBD symptoms, including weight loss and the production of loose, bloody stools. The intensity of the disease progressively increased from Day 4 to the time the mice were sacrificed on Day 6. Treatment of the animals receiving DSS with ABC294640, ABC747080 or Dipentum reduced the intensity of the IBD manifestations in the mice, most dramatically on Day 6. The SK inhibitors and Dipentum were essentially equivalent in their abilities to reduce the DAI of mice receiving DSS. It should be noted that this acute model produces rapid and dramatic symptoms of IBD, making it a very stringent assay for drug testing.

Figure 7:
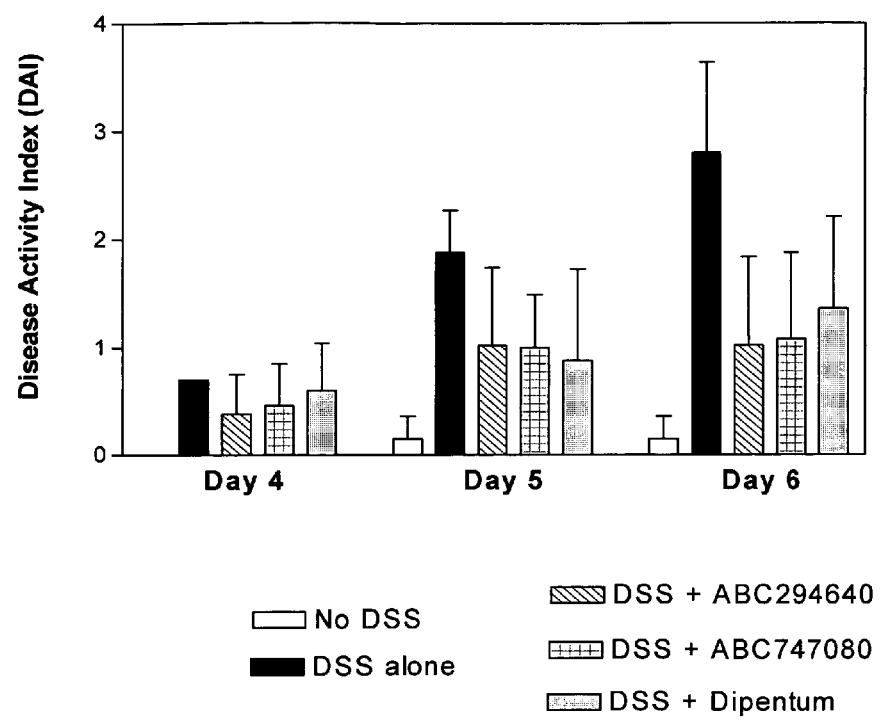
FIG. 7. Effects of SK inhibitors and Dipentum on the DAI in the acute DSS-colitis model. C57BL/6 mice were treated for 6 days as follows: normal drinking water and daily oral administration of PEG (No DSS), 2% DSS in the drinking water and daily oral administration of PEG (DSS alone); 2% DSS in the drinking water and daily oral administration of 50 mg/kg ABC294640 in PEG (DSS+ABC294640), 2% DSS in the drinking water and daily oral administration of 50 mg/kg ABC747080 in PEG (DSS+ABC747080), 2% DSS in the drinking water and daily oral administration of 50 mg/kg Dipentum in PEG (DSS+Dipentum). On the indicated day, the Disease Activity Index was calculated for each group. Values represent the mean±sd for 5-6 mice per group.
Figure 8:
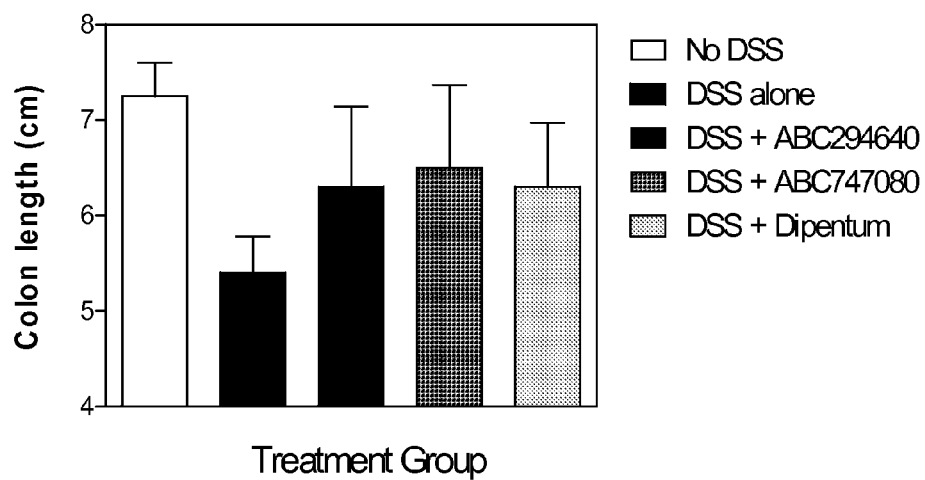
FIG. 8. Effects of SK inhibitors and Dipentum on colon length in the acute DSS-colitis model. Mice from the experiment described in FIG. 7 were sacrificed on Day 6, and the colon was harvested from each animal and measured. Data represent the mean±sd colon length.

On Day 6, the animals were sacrificed by cervical dislocation and the entire colon was measured to assess shortening due to scarring and damage, and then fixed, sectioned and examined histologically on a blinded basis. Compared with the water control group, the colons of mice treated with DSS and PEG were significantly shortened (FIG. 7). DSS-treated mice that were also treated with ABC294640, ABC747080 or Dipentum had colons of intermediate length, indicating substantial protection by the drugs. Again, the response to either of the SK inhibitors was at least as good as that of mice treated with Dipentum.

Histological examination of colon sections from the various treatment groups were consistent with the DAI endpoint, revealing marked damage in the DSS-alone group that was reduced or negated in the SK inhibitor-treated animals. Colons from water-treated control animal demonstrated normal morphology, while colons from DSS alone-treated mice were severely inflamed and damaged. Numerous neutrophils were present throughout the section, along with severely damaged crypts, and moderate inflammatory infiltration with submucosal edema. Colons from animals treated with DSS and ABC294640 showed no or mild crypt damage, no or low levels of inflammatory cell infiltration and no edema in the submucosa.

Figure 9:
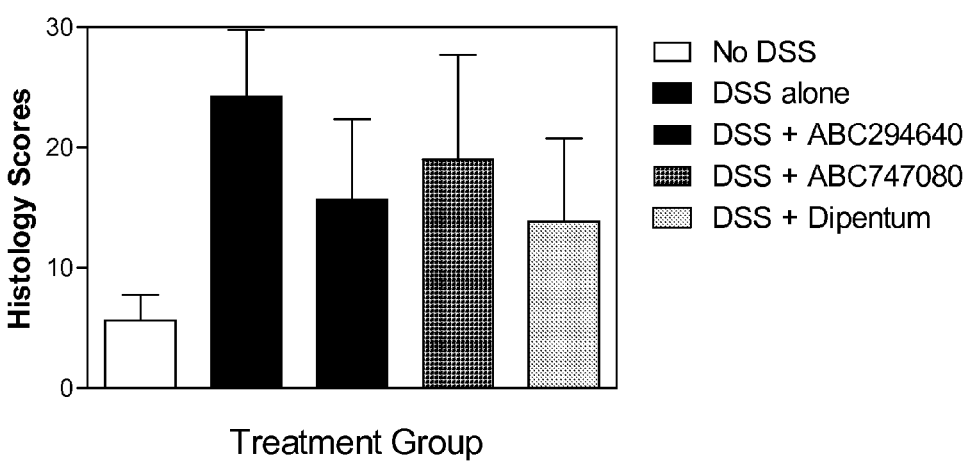
FIG. 9. Effects of SK inhibitors and Dipentum on the colon Histology Score in the acute DSS-colitis model. Mice from the experiment described in FIG. 7 were sacrificed on Day 6, and the colon was harvested from each animal and the Histology Score was determined. Values represent the mean±sd for 5-6 mice per group.

As a quantifiable measure of damage, the colons were graded for their Histology Score, which is based on inflammation severity, inflammation extent, crypt damage and the percentage of surface area demonstrating the characteristic. These morphologies were scored on a blinded basis. As indicated in FIG. 9, animals receiving DSS in their drinking water had substantially higher Histology Scores (representing moderate-to-severe IBD) than animals receiving normal drinking water (which had some mild inflammation, possibly due to the PEG vehicle). As with the other assays, the Histology Scores of mice given an SK inhibitor or Dipentum were consistently lower than the DSS-alone animals, although not all animals were fully protected. DAI scores and histology scores correlated well for the individual animals, confirming that the DAI score as an excellent indicator of colon inflammation and damage.

Figure 10:
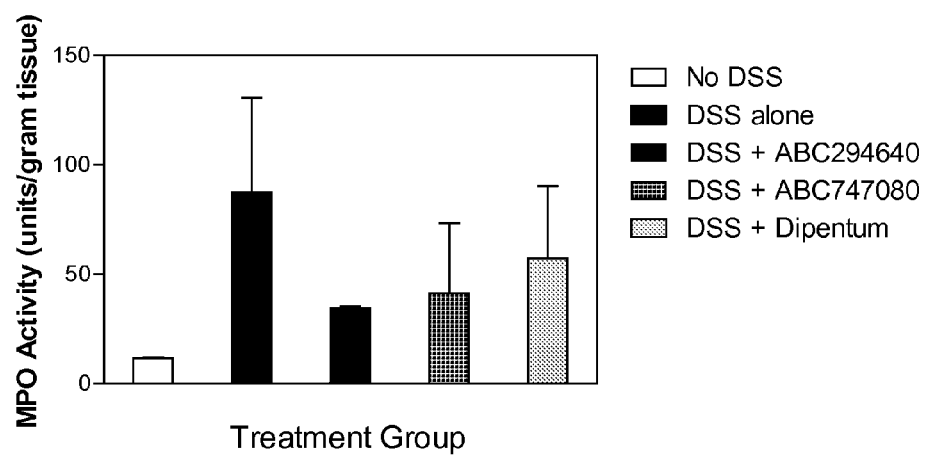
FIG. 10. Effects of SK inhibitors and Dipentum on neutrophil infiltration into the colon in the acute DSS-colitis model. Myeloperoxidase activity from the colons of the animals described in FIG. 7 was measured. Values the mean±sd MPO activity in units per gram of tissue.

Myeloperoxidase (MPO) activity, which is reflective of neutrophil influx into the colon, is often used as measure of inflammation, and was assayed in the colons of the mice from the DSS-colitis studies. As indicated in FIG. 10, MPO activity was highly elevated in the DSS-alone animals compared to water controls. The increase in MPO activity was markedly attenuated in mice receiving daily doses of ABC294640, ABC747080 or Dipentum. This reduction in the activity of the neutrophil marker is consistent with the decreased occurrence of granulocytes observed in the H&E-stained colon sections. Therefore, the level of colonic MPO appears to be an excellent biomarker for the extent of tissue infiltration by inflammatory leukocytes.

Figure 11:
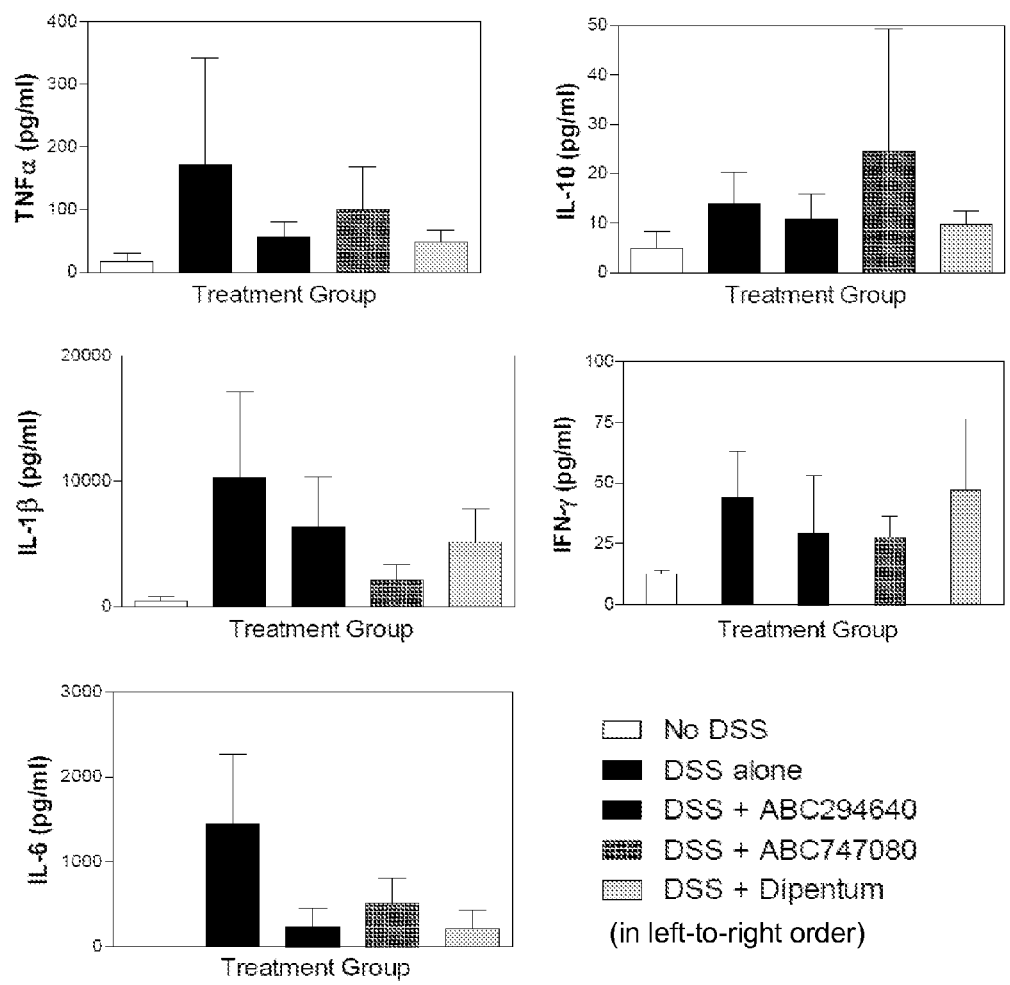
FIG. 11. Effects of SK inhibitors and Dipentum on colonic cytokine levels in the acute DSS-colitis model. Colon samples from mice described in FIG. 7 were extracted and assayed for the levels of the indicated cytokines. Values represent the mean±sd amount of each cytokine in 4-5 samples per group.

Several cytokines involved in inflammation were measured using the Luminex 100 System that allows the quantification of multiple cytokines and growth factors in a small sample volume. We examined the Th1 cytokine IFN-γ, the regulatory IL-10 cytokine, as well as the macrophage-derived pro-inflammatory cytokines, TNFα, IL-1β, IL-6 in colon samples from mice in the DSS model of colitis. FIG. 11 depicts the results of these assays, and indicates that DSS-treatment promoted the accumulation of all of the cytokines in the colon. Importantly, the elevations of all of the pro-inflammatory proteins, i.e. IFN-γ, IL-1β, IL-6 and TNFα, were attenuated in mice treated with either an SK inhibitor or Dipentum. Conversely, levels of the anti-inflammatory cytokine IL-10 were not suppressed by the SK inhibitors.

Figure 12:
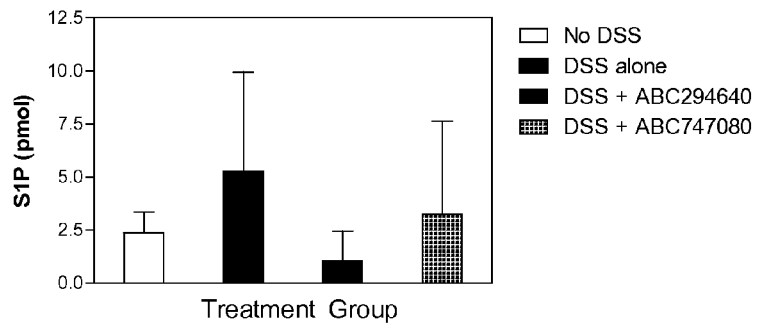
FIG. 12. Effects of SK inhibitors on S1P levels in the colons of the animals in the DSS-colitis model. Colon samples from mice described in FIG. 7 were extracted and assayed for the levels of S1P by LC/MS/MS. Values represent the mean±sd for 4-5 samples per group.

As a final measure of the effects of the SK inhibitors in this acute model, S1P levels were assayed in the colons of the DSS-treated animals using an LC-MS/MS method. This technique allows us to examine correlations between biologic activity and changes in S1P levels in animals treated with the SK inhibitors. Samples of colons from animals from the DSS-colitis experiments were homogenized in cold PBS, spiked with internal standards ($C_{17}$ analogs of sphingosine and S1P) and processed by liquid-liquid extraction. Ratios of analyte to internal standard for each sphingolipid were determined. S1P levels were markedly higher in the colons from DSS-treated mice as compared to the water controls (FIG. 12). Importantly, animals that were treated with either ABC294640 or ABC747080 had markedly lower levels of colonic S1P than the DSS-alone samples.

EXAMPLE 10

In Vivo Effects of SK Inhibitors in a Chronic Model of Inflammatory Bowel Disease A 35-day model of IBD was used to evaluate the effectiveness of the SK inhibitors in mice that experience multiple cycles of DSS-induced inflammation. This chronic model is similar to the acute model, except that the DSS concentration in the drinking water is lower and animals receive periodic exposure to DSS (DSS on days 1-7, water on Days 8-13, DSS on day 14-21, water on Days 22-27 and then DSS until the completion of the study on Day 35). In these experiments, treatment of the mice with an SK inhibitor or Dipentum began on Day 28 and continued daily until the completion of the study. The DAI index was monitored every other day until Day 28 and then daily until Day 35. Animals were sacrificed on Day 35, and changes in the colon length and cytokine profiles were measured.

Figure 13:
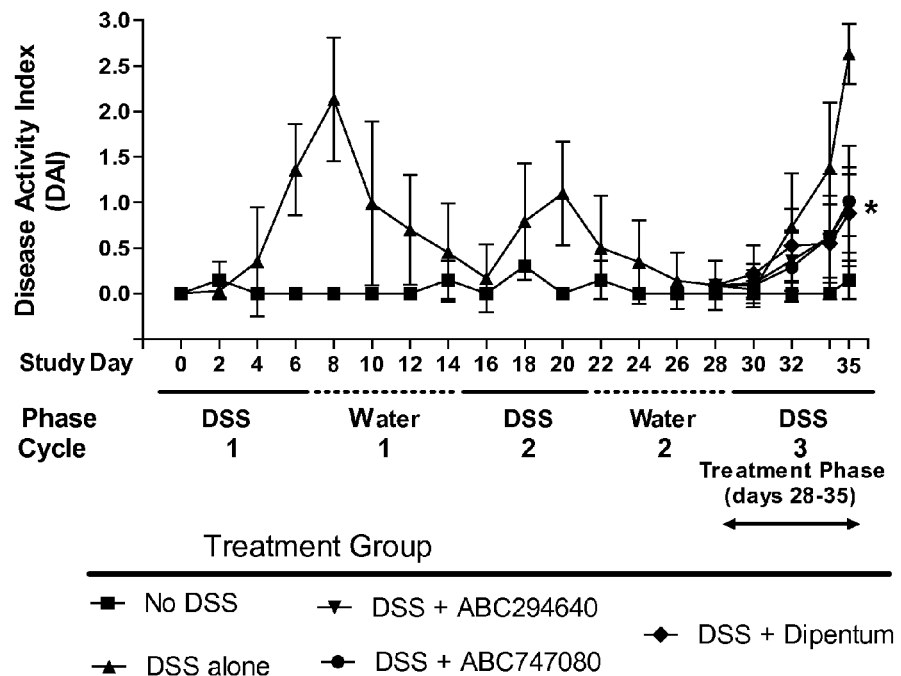
FIG. 13. Effects of SK inhibitors on the DAI in the chronic DSS-colitis model. Mice received 2 cycles (7 days per cycle) of DSS (1.5% cycle 1 and 1% cycle 2), 2 cycles of normal drinking water and were randomized by DAI on Day 28 into groups of 8 mice. The mice were then treated as follows: No DSS (■)—normal drinking water and orally dosed with PEG400 every day for 7 days (water control); DSS alone (▲)—drinking water containing 1.5% DSS and orally dosed with PEG daily for 7 days; DSS+ABC294640 (▼)—drinking water containing 1.5% DSS and orally dosed with ABC294640 (50 mg/kg) every day for 7 days; DSS+ABC747080 (●)—drinking water containing 1.5% DSS and orally dosed with ABC747080 (50 mg/kg) daily for 7 days; DSS+Dipentum (♦)—drinking water containing 1.5% DSS and orally dosed with Dipentum (50 mg/kg). *p<0.001 versus No DSS group.

Cyclic exposure of mice to DSS in their drinking water caused reversible increases in the DAI (FIG. 13). Treatment of the mice with ABC294640, ABC747080 or Dipentum during the third exposure to DSS significantly suppressed the increase in DAI experienced by the control mice (P<0.001 for all three compounds on Day 35).

The colon lengths of DSS-treated mice were significantly shorter than the water-treated control animals (4.9±0.2 cm vs. 7.8±0.3 cm) reflecting inflammation-induced scarring. As in the acute model, the colons of animals treated with ABC294640, ABC747080 or Dipentum were of intermediate length (6.2±0.2, 5.8±0.1 and 6.1±0.2 cm, respectively). This is a significant finding since the animals were untreated for the first and second DSS cycles. Therefore, suppression of inflammation-induced colon contraction can be reversed by effective anti-IBD drugs.

Immunohistochemistry revealed that SK expression was present in low levels in the colons of control, non-DSS treated mice. SK expression was elevated in the colons of DSS treated mice compared to water controls with this expression clearly reduced in DSS mice also receiving compound ABC292640.

Figure 14:
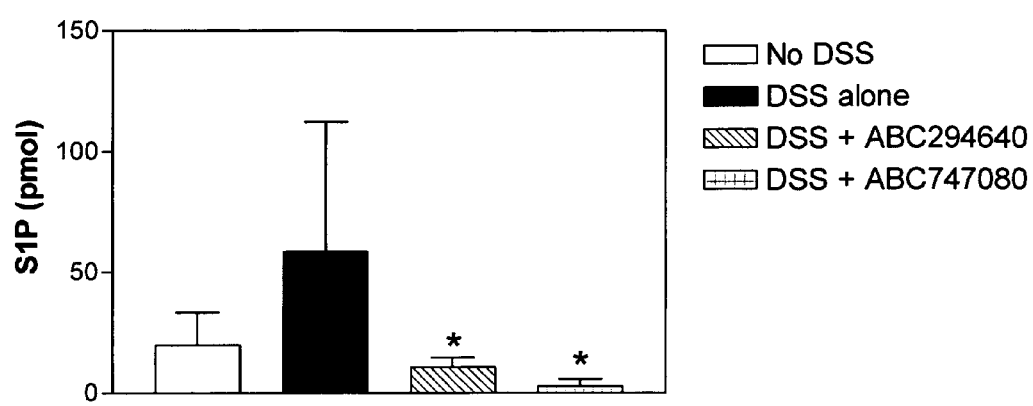
FIG. 14. Effects of SK inhibitors on S1P levels in the colons of the animals in the chronic DSS-colitis model. Colon samples from mice described in FIG. 13 were extracted and assayed for the levels of S1P by LC/MS/MS. Values represent the mean±sd for 8 samples per group; *p<0.05 versus No DSS group.

S1P levels in the colons of the chronic colitis model mice were assessed in an identical manner as described for the acute model, and revealed results similar to those in the acute model with elevated S1P levels in DSS alone treated mice as compared to water controls (FIG. 14). Treatment with compounds ABC29460 and ABC747080 (oral 50 mg/kg daily; 7 days prior to sacrifice) resulted in significant reductions of S1P levels (FIG. 14).

Figure 15:
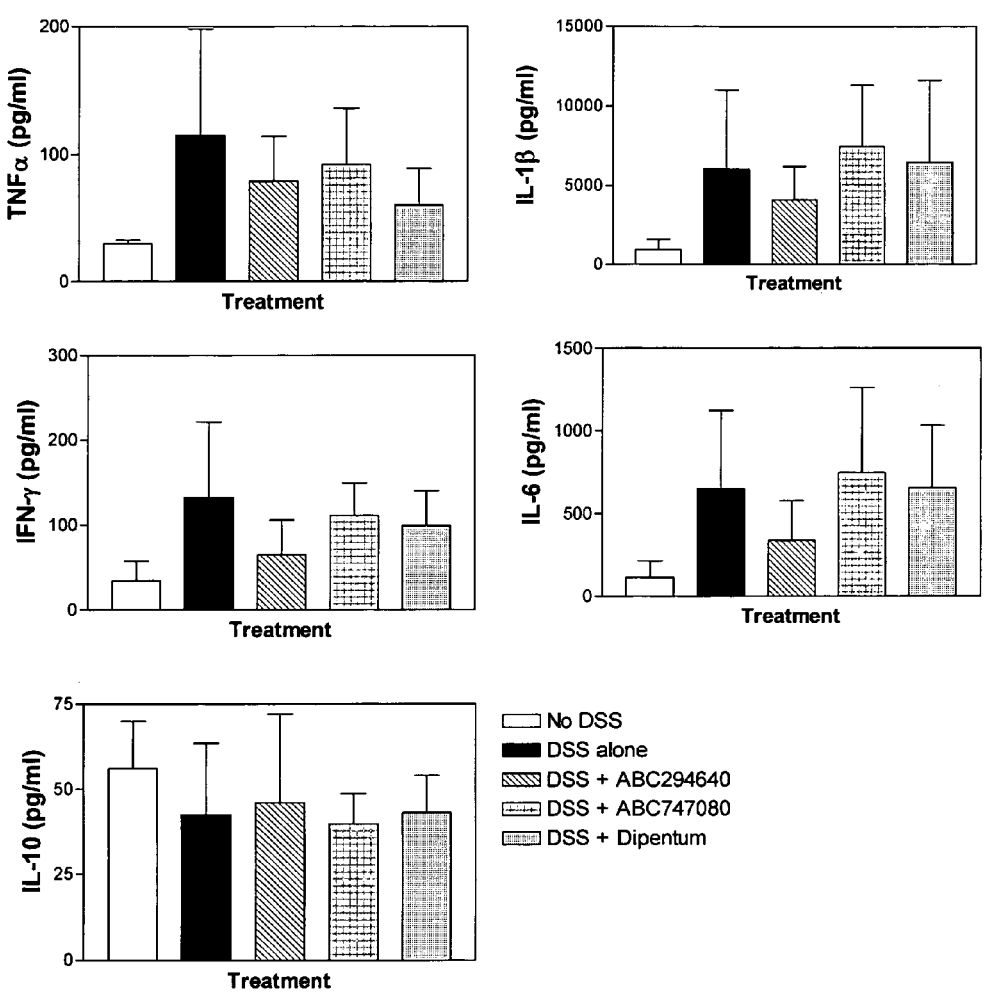
FIG. 15. Effects of SK inhibitors and Dipentum on colonic cytokine levels in the chronic DSS-colitis model. Colon samples from mice described in FIG. 13 were extracted, and assayed for the levels of the indicated cytokines. Values represent the mean±SD amount in 8 samples per group.

The levels of the pro-inflammatory cytokines TNFα, IL-1β, IFN-γ and IL-6 were substantially increased in the colons of mice treated chronically with DSS; whereas, the level of IL-10 was unchanged (FIG. 15). Mice treated with ABC294640 during the final DSS cycle had reduced levels of the pro-inflammatory cytokines, while animals treated with ABC747080 or Dipentum expressed cytokine profiles equivalent to the DSS-alone group. This may reflect the presence of high numbers of resident immune cells in the colons of mice exposed chronically to DSS. However, the elevation in cytokine levels in the SK inhibitor-treated mice does not result in increased DAI or colon shortening, indicating that signaling induced by the inflammatory cytokines had been blocked.

Figure 16:
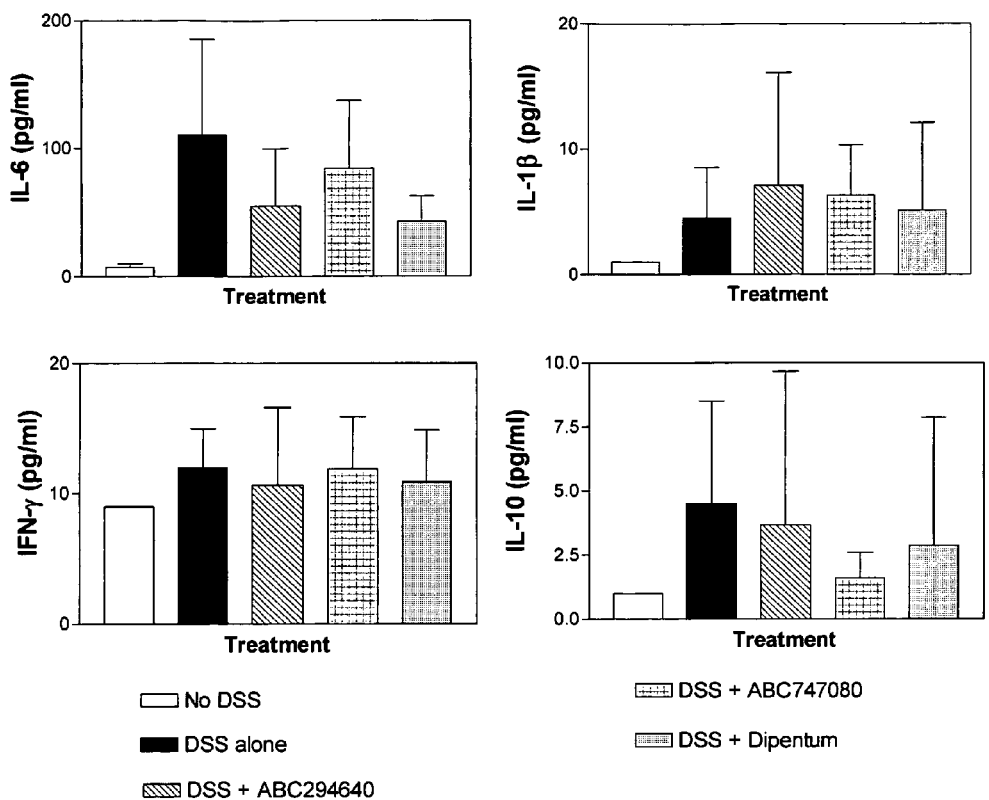
FIG. 16. Effects of SK inhibitors and Dipentum on serum cytokine levels in the chronic DSS-colitis model. Serum from mice described in FIG. 13 was assayed for the levels of the indicated cytokines. Values represent the mean±SD amount in 8 samples per group.

For comparison, the levels of the same cytokines in the serum of the mice at the time of sacrifice were also determined. As indicated in FIG. 16, the circulating levels of these cytokines are markedly lower than the colonic levels reflecting the local inflammation in this model. DSS increased the circulating levels of IL-1β, IFN-γ, IL-6 and IL-10, while TNFα remained below the detection limit of the assay. None of the test compounds affected the circulating levels of IL-1β or INF-γ; however, both ABC294640 and Dipentum reduced the serum level of IL-6. Therefore, serum levels of IL-6 may be a useful pharmacodynamic marker for the anti-inflammatory effects of the SK inhibitors during clinical testing.

EXAMPLE 11

In Vivo Effects of SK Inhibitors in the Collagen-Induced Arthritis Model in Mice The anti-arthritis activities of the SK inhibitors ABC294640 and ABC747080 were assessed in the Collagen-Induced Arthritis (CIA) model. Female DBA/1 mice were injected subcutaneously in the tail with chicken immunization-grade type II collagen (Chondrex) emulsified in complete Freund's adjuvant (Sigma) at 2 mg/mL. Three weeks later, the mice received a collagen booster in incomplete Freund's adjuvant and were monitored daily thereafter for arthritic symptoms. Once mice reached a threshold paw thickness and clinical score, they were randomized into the following treatment groups: ABC294640 (100 mg/kg given orally each day for 6 days per week), ABC747080 (50 mg/kg given orally each day for 6 days per week) or vehicle (0.375% Tween-80 given under the same schedule). The severity of disease in each animal was quantified by measurement of the hind paw volume with digital calipers. Each paw was scored based upon perceived inflammatory activity, in which each paw receives a score of 0-3 as follows: 0=normal; 1=mild, but definite redness and swelling of the ankle or wrist, or apparent redness and swelling limited to individual digits, regardless of the number of affected digits; 2=moderate redness and swelling of the ankle and wrist and 3=severe redness and swelling of the entire paw including digits, with an overall score ranging from 0-12. Differences among treatment groups were tested using ANOVA.

Figures 17A, 17B:
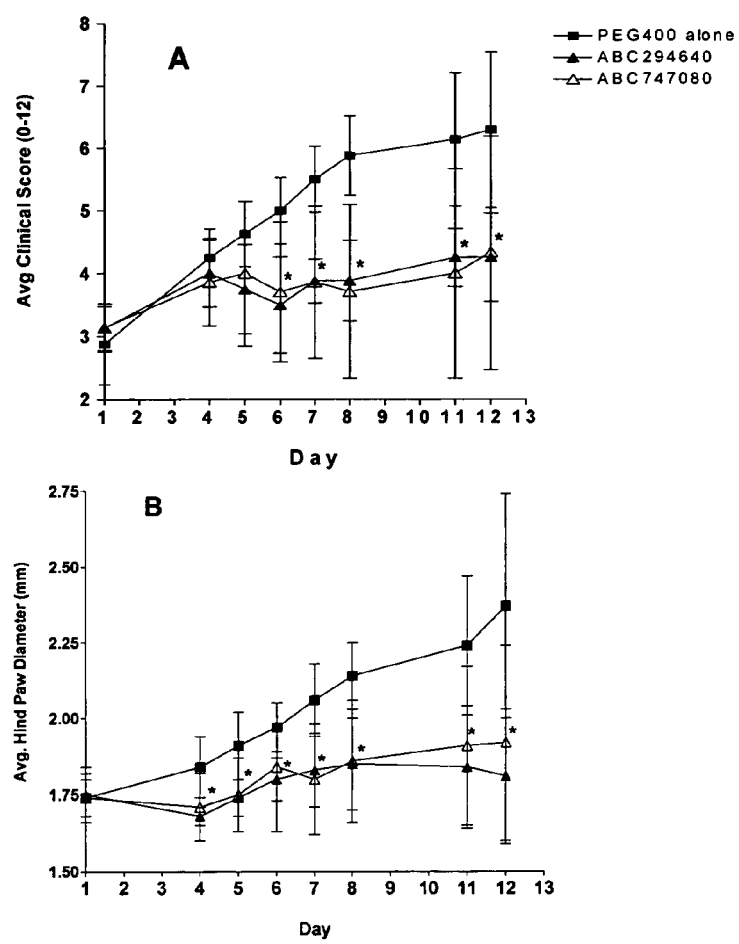
FIG. 17. Effects of SK inhibitors on disease progression in the CIA model in mice. Female DBA/1 mice were injected with collagen, boosted after 3 weeks and then monitored for symptoms of arthritis. Upon disease manifestation, groups of mice were treated for 12 days as follows: (▲) ABC294640 (100 mg/kg given orally each day for 6 days per week); (Δ) ABC747080 (50 mg/kg given orally each day for 6 days per week); or (■) vehicle (PEG400 given under the same schedule). On the indicated Day of treatment, the average clinical score (A) and the average hind paw diameter (B) was determined. *p≦0.05 versus PEG400 alone group.

As indicated in FIG. 17, treatment with either SK inhibitor dramatically slowed the inflammation response, measured as either the Average Clinical Score (FIG. 17A) or the Average Hind Paw Diameter (FIG. 17B), with significant decreases beginning at Day 5 of treatment for both endpoints. By the end of the experiment on Day 12, ABC294640 caused a 90% reduction in the increase in hind paw thickness, and a 67% reduction in clinical score compared with vehicle-treated mice. Similarly, ABC747080 caused a 72% reduction in the increase in hind paw thickness, and a 65% reduction in clinical score. Since a 30% reduction in symptoms is considered demonstrative of anti-arthritic activity in this assay, these SK inhibitors surpass the criteria for efficacy in this model.

On Day 12, the mice were euthanized and their hind limbs were removed, stripped of skin and muscle, formalin-fixed, decalcified and paraffin-embedded. The limbs were then sectioned and stained with hematoxylin/eosin. Tibiotarsal joints were evaluated histologically for severity of inflammation and synovial hyperplasia. Collagen-Induced Arthritis resulted in a severe phenotype compared with non-induced mice, manifested as severe inflammation and synovial cell infiltration, as well as significant bone resorption. Mice that had been treated with either ABC294640 or ABC747080 had significantly reduced histologic damage, correlating with the paw thickness and clinical score data.

EXAMPLE 12

In Vivo Effects of SK Inhibitors in the Adjuvant-Induced Arthritis Model in Rats Adjuvant-induced arthritis is another widely used assay that recapitulates many features of human rheumatoid arthritis, and so is useful in the evaluation of new drug candidates. Age- and weight-matched male Lewis rats (150-170 g) were injected subcutaneously in the tail with 1 mg of *Mycobacterium butyricum* (Difco, killed dried) suspended in 0.1 ml of light mineral oil. Symptoms of immune reactivity were present after 2 weeks. Responsive rats were randomized into treatment groups, and received oral daily doses (1 ml) of: solvent alone (0.375% Tween-80); 100 mg/kg ABC294640; 35 mg/kg ABC294640; or 5 mg/kg ABC294640, or intraperitoneal injections of indomethacin (5 mg/kg) every other day as a positive control. The severity of disease in each animal was quantified by measurement of the hind paw thickness. As above, a reduction of 30% or greater was considered to be an indication of anti-inflammatory activity in this model.

Figures 18A, 18B, 18C:
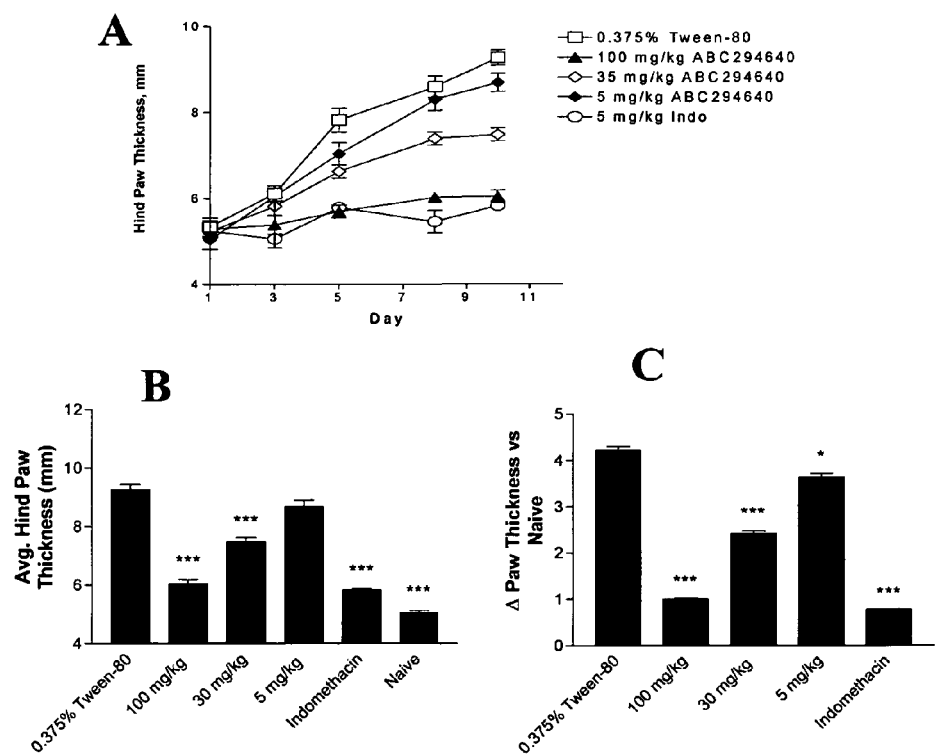
FIG. 18. Effects of ABC294640 on disease progression in the adjuvant-induced arthritis model in rats. Male Lewis rats were injected subcutaneously with *Mycobacterium butyricum*, and symptoms of immune reactivity were present after 2 weeks. Responsive rats were randomized into treatment groups (n=8 per group), and received oral daily doses of: solvent alone (0.375% Tween-80); 100 mg/kg ABC294640; 35 mg/kg ABC294640; or 5 mg/kg ABC294640, or intraperitoneal injections of indomethacin (5 mg/kg) every other day. The severity of disease in each animal was quantified by measurement of the hind paw thickness. Panel A. Time course of hind paw arthritic response. Panel B. Final day (Day 10) hind paw thickness measurements. Panel C. Change in paw thickness of respective group versus non-arthritic rats (naive) at Day 10. *, p<0.05; ***, p<0.001 versus solvent alone group.

As indicated in FIG. 18, solvent alone-treated rats demonstrated a progressive increase in paw thickness over the course of the next 10 days. ABC294640 inhibited this arthritic response in a dose-dependent manner, with the highest dose having similar therapeutic efficacy as indomethacin. ABC294640 at doses of 5, 35 or 100 mg/kg resulted in 13, 42 and 76 percent reductions in the arthritic response, respectively. Thus, ABC294640 is highly effective against this arthritis model.

We claim:

1. A method for treating an inflammatory disease comprising delivering to a patient a sphingosine kinase inhibitor compound or pharmaceutical composition comprising a sphingosine kinase inhibitor in an amount effective to inhibit sphingosine kinase activity, wherein the sphingosine kinase inhibitor is selected from the group consisting of

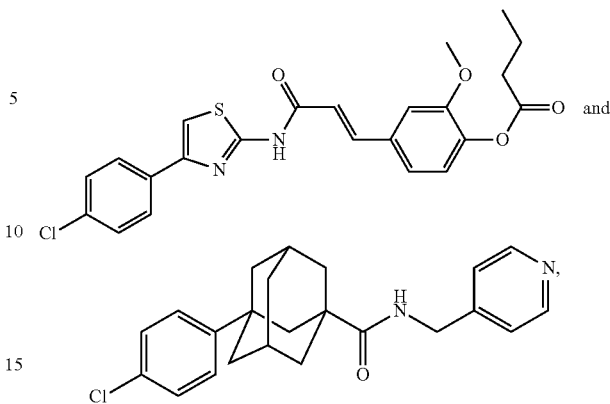

wherein the inflammatory disease is selected from the group consisting of inflammatory bowel disease, arthritis, atherosclerosis, and asthma.

2. A method of claim 1 wherein said inflammatory disease is an inflammatory bowel disease is selected from the group consisting of ulcerative colitis, Crohn's Disease and indeterminate colitis.

3. A method of claim 2, wherein the sphingosine kinase inhibitor compound or composition comprising a sphingosine kinase inhibitor is delivered in an amount effective to inhibit the aberrant activation of luminal eplithial cells, macrophages, mast cells or neutrophils.

4. A method of claim 1, wherein said sphingosine kinase inhibitor compound is

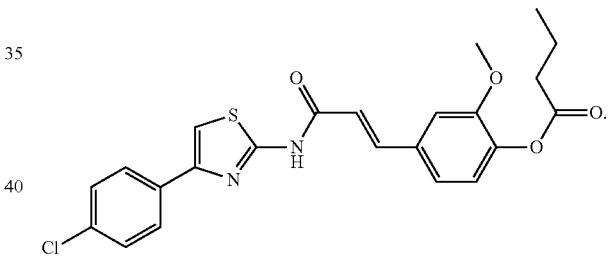

5. A method of claim 1, wherein said sphingosine kinase inhibitor compound is

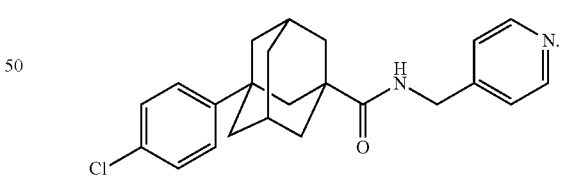

6. A method of claim 1, wherein said inflammatory disease is an inflammatory bowel disease.

7. A method of claim 1, wherein said inflammatory disease is arthritis.

8. A method of claim 1, wherein said inflammatory disease is atherosclerosis.

9. A method of claim 1, wherein said inflammatory disease is asthma.

10. A method of claim 1, wherein said inflammatory disease is associated with excessive TNFα activity.

* * * * *